US006946270B1

(12) United States Patent
Hashimoto et al.

(10) Patent No.: US 6,946,270 B1
(45) Date of Patent: Sep. 20, 2005

(54) PROCESS FOR PRODUCING HMG-COA REDUCTASE INHIBITORS

(75) Inventors: Shin-ichi Hashimoto, Hofu (JP); Yoshiyuki Yonetani, Machida (JP); Akio Ozaki, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/868,924

(22) PCT Filed: Jan. 20, 2000

(86) PCT No.: PCT/JP00/00245

§ 371 (c)(1),
(2), (4) Date: Oct. 31, 2001

(87) PCT Pub. No.: WO00/43533

PCT Pub. Date: Jul. 27, 2000

(30) Foreign Application Priority Data

Jan. 20, 1999 (JP) .......................................... 11/012392

(51) Int. Cl.[7] .............................................. C12P 17/06
(52) U.S. Cl. ........................ 435/125; 435/136; 435/146; 435/155; 435/132
(58) Field of Search ............................... 435/125, 136, 435/146, 155, 132

(56) References Cited

U.S. PATENT DOCUMENTS

| | | | |
|---|---|---|---|
| 4,346,227 A | | 8/1982 | Terahara et al. |
| 4,410,629 A | | 10/1983 | Terahara et al. |
| 4,448,979 A | | 5/1984 | Terahara et al. |
| 4,537,859 A | | 8/1985 | Terahara et al. |
| 5,942,423 A | * | 8/1999 | Demain et al. ............. 435/125 |
| 6,043,064 A | | 3/2000 | Davis et al. |
| 6,245,535 B1 | | 6/2001 | Takano et al. |

FOREIGN PATENT DOCUMENTS

| | | |
|---|---|---|
| EP | 0649907 | 4/1995 |
| EP | 1148122 | 10/2001 |
| JP | 57-50894 | 3/1982 |
| JP | 64-2585 | 1/1989 |
| JP | 7-184670 | 7/1995 |
| JP | 2672551 | 7/1997 |
| WO | 96/40863 | 12/1996 |
| WO | 99/07872 | 2/1999 |
| WO | 99/10499 | 3/1999 |
| WO | WO 99/60151 | * 11/1999 |
| WO | 00/44886 | 8/2000 |

OTHER PUBLICATIONS

Okazaki T, et al. Taxonomy of actinomycetes capable of hydroxylation of ML–236B (compactin). J. Antibiot. 36: 1176–1183, 1983.*
ATCC website: http://www.atcc.org/SearchCatalogs/Bacteria.cfm.*
The Journal of Antibiotics, vol. 29, p. 1346 (1976).
English Language Abstract of JP 57–50894.
English Language Abstract of JP 7–184670.
English Language Abstract of JP 64–2585.

P.F. Stansbury et al., Basic Fermentation Technology (Hakko Kogaku no Kiso),pp. 169–190(Japan Scientific Societies Press 1988).
Sankyo Research Laboratories Annual Report, vol. 37, p. 147 (1985).
N. Serizawa et al., Biochemical and Molecular Approaches for Production of Prevastatin, a Potent Chololesterol–Lowering Drug, Biotech. Ann Rev., vol. 2, pp. 373–389 (1996).
A. Witkowski et al., Biochemistry, vol. 38, 1999, pp. 11643–11650.
J.L. Seffernick et al., Journal of Bacteriology, vol. 183, No. 8, Apr. 2001, pp. 2405–2410.
"Gene Name Search with the Pattern 'yjiB'", downloaded from http://www.pasteur.fr/Bio/SubtiList.html.
F. Kunst et al., Nature, vol. 390, 1997, pp. 249–256.
A. Alberts, Cardiology, vol. 77 (suppl. 4), 1990, pp. 14–21.
C. Rivolta et al., Microbiology, vol. 144, 1998, pp. 877–884.
U.S. Appl. No. 09/869,334 to ENDO et al., filed Sep. 26, 2001.

* cited by examiner

Primary Examiner—Irene Marx
(74) Attorney, Agent, or Firm—Greenblum & Bernstein, P.L.C.

(57) ABSTRACT

The present invention relates to a process for producing a compound (II-a) or a compound (II-b), each of which is a hydroxylated product of a compound represented by the formula (I-a) (hereinafter referred to as compound (I-a)):

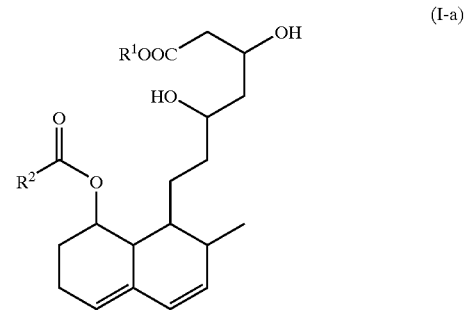

(I-a)

wherein
$R^1$ represents a hydrogen atom, a substituted or unsubstituted alkyl, or an alkali metal, and $R^2$ represents a substituted or unsubstituted alkyl, or a substituted or unsubstituted aryl;
or a ring-closed lactone form thereof (hereinafter referred to as compound (I-b)).
wherein the process comprises:
treating the compound (I-a) or compound (I-b) in an aqueous medium comprising with a microorganism acting to hydroxylate compound (I-a) or compound (I-b), having no ability to sporulate and showing no hyphal growth, a culture of the microorganism, or a treated product of the culture, as an enzyme source; and
collecting a hydroxylated product of compound (I-a) or compound (I-b) from the aqueous medium.

7 Claims, No Drawings

PROCESS FOR PRODUCING HMG-COA REDUCTASE INHIBITORS

TECHNICAL FIELD

The present invention relates to a process for producing a compound, which inhibits hydroxymethylglutaryl CoA (HMG-CoA) reductase and has an action of reducing serum cholesterol.

BACKGROUND ART

A compound represented by the formula (VI-a) (hereinafter referred to as compound (VI-a)):

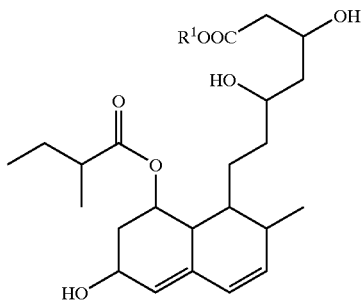

(VI-a)

wherein $R^1$ represents a hydrogen atom or an alkali metal, or a lactone form of compound (VI-a) represented by the formula (VI-b) (hereinafter referred to as compound (VI-b)):

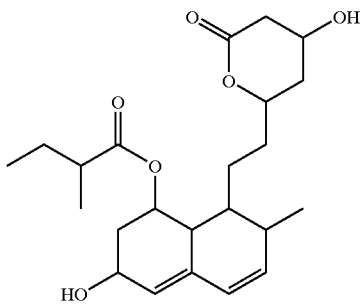

(VI-b)

is known to inhibit HMG-CoA reductase and exhibit an action of reducing serum cholesterol and the like (*The Journal of Antibiotics*, 29, 1346 (1976)).

There have been several reports regarding a method for producing the compound (VI-a) or the compound (VI-b) from a compound represented by the formula (V-a) (hereinafter referred to as compound (V-a)):

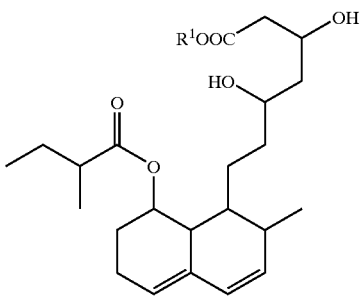

(V-a)

wherein $R^1$ represents a hydrogen atom or an alkali metal, or the lactone form of compound (V-a) represented by the formula (V-b) (hereinafter referred to as compound (V-b)):

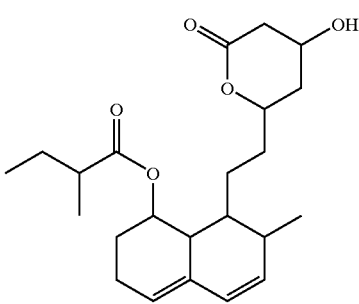

(V-b)

using a microorganism.

Specifically, Japanese Patent Application Laid-Open (kokai) No. 57-50894 describes a method which uses filamentous fungi; both Japanese Patent Application Laid-Open (kokai) No. 7-184670 and International Publication WO96/40863 describe a method which uses *Actinomycetes*; and Japanese Patent No. 2672551 describes a method which uses recombinant *Actinomycetes*. As is well known, however, since filamentous fungi and *Actinomycetes* grow with filamentous form by elongating hyphae, the viscosity of the culture in a fermentor increases. This often causes shortage of oxygen in the culture, and since the culture becomes heterogeneous, reaction efficiency tends to be reduced. In order to resolve this oxygen shortage and maintain homogeneousness of the culture, the agitation rate of the fermentor should be raised, but by raising the agitation rate, hyphae are sheared and activity of the microorganisms tends to decrease (Basic Fermentation Engineering (Hakko Kogaku no Kiso) p. 169–190, P. F. Stansbury, A. Whitaker, Japan Scientific Societies Press (1988)).

Furthermore, the above *Actinomycetes* and filamentous fungi have an ability to sporulate. Since spores tend to disperse much more easily than cells and have an ability of surviving even under conditions where vegetative cells perish readily, these spores tend to become a source of microorganism contamination in culturing and purification processes.

DISCLOSURE OF THE INVENTION

The object of the present invention is to provide an industrially advantageous method for producing a compound which inhibits HMG-CoA reductase and has an action of reducing the level of serum cholesterol and the like.

The present inventors have considered that if hydroxylation of compound (V-a) or compound (V-b) could be carried out with a microorganism having hydroxylation activity, having no ability to sporulate and showing no hyphal growth, inconvenience such as the decrease of reaction efficiency due to microorganism contamination caused by the release of spores during the production process or the heterogeneity of the culture caused by formation of hyphae could be avoided, and that this would be industrially advantageous. As a result of intensive studies directed to this object, the present inventors have accomplished the present invention.

Thus, the present invention relates to the following (1) to (9).

Hereinafter, in the formulas, $R^1$ represents a hydrogen atom, a substituted or unsubstituted alkyl, or an alkali metal, and $R^2$ represents a substituted or unsubstituted alkyl, or a substituted or unsubstituted aryl, unless otherwise specified.

(1) A process for producing a compound (II-a) or a compound (II-b) wherein a microorganism having an activity of producing compound (II-a) or a compound (II-b) from a compound (I-a) or a compound (I-b), having no ability to sporulate and showing no hyphal growth, a culture of said microorganism, or a treated product of said culture is used as an enzyme source, and the process comprises: allowing the compound (I-a) or the compound (I-b) to exist in an aqueous medium; allowing the compound (II-a) or the compound (II-b) to be produced and accumulated in said aqueous medium; and collecting the compound (II-a) or the compound (II-b) from said aqueous medium, and wherein the compound (I-a) is a compound represented by the formula (I-a) (herein referred to as compound (I-a)):

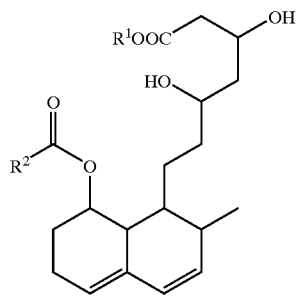

(I-a)

the compound (I-b) is a lactone form of compound (I-a) represented by the compound (I-b) (herein referred to as compound (I-b)):

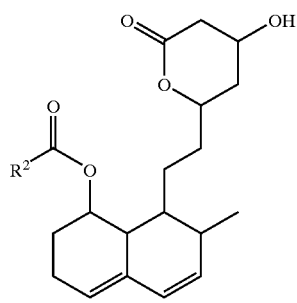

(I-b)

the compound (II-a) is a compound represented by the formula (II-a) (herein referred to as compound (II-a)):

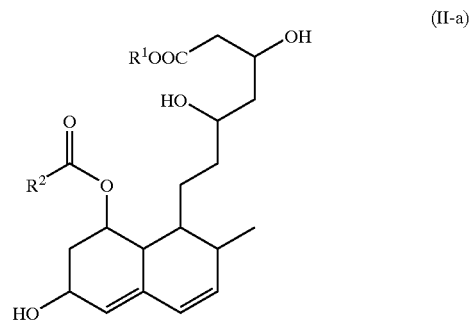

(II-a)

and the compound (II-b) is a lactone form of compound (II-a) represented by the formula (II-b) (herein referred to as compound (II-b)):

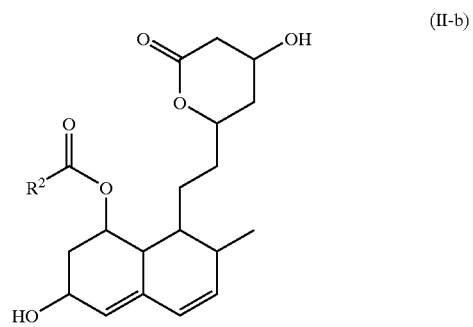

(II-b)

(2) The process according to (1) above, wherein the compound (I-a) is a compound represented by the formula (III-a) (herein referred to as compound (III-a)):

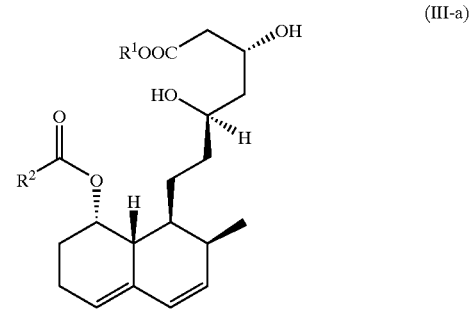

(III-a)

the compound (I-b) is a compound represented by the formula (III-b) (herein referred to as compound (III-b)):

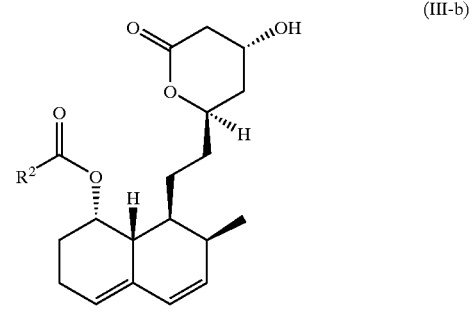

(III-b)

the compound (II-a) is a compound represented by the formula (IV-a) (herein referred to as compound (IV-a)):

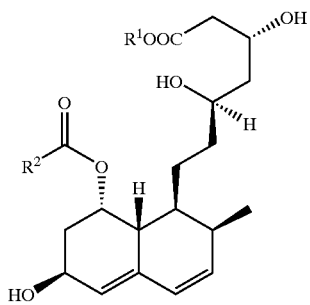
(IV-a)

the compound (II-b) is a compound represented by the formula (IV-b) (herein referred to as compound (IV-b)):

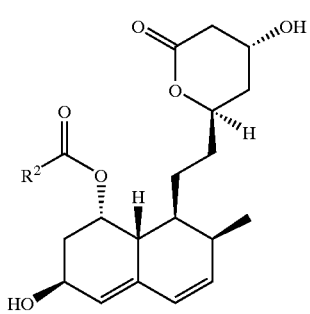
(IV-b)

(3) The process according to (1) above, wherein the compound (I-a) is a compound represented by the formula (V-a) (herein referred to as compound (V-a)):

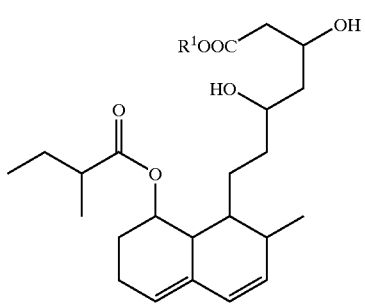
(V-a)

the compound (I-b) is a compound represented by the formula (V-b) (herein referred to as compound (V-b)):

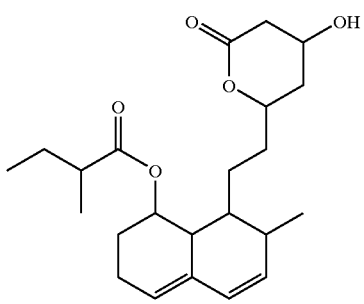
(V-b)

the compound (II-a) is a compound represented by the formula (VI-a) (herein referred to as compound (VI-a)):

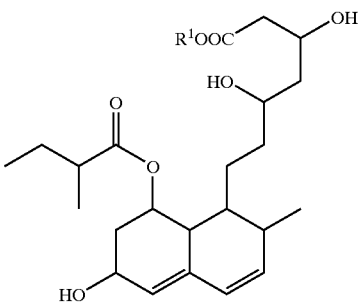
(VI-a)

and; the compound (II-b) is a compound represented by the formula (VI-b) (herein referred to as compound (VI-b)):

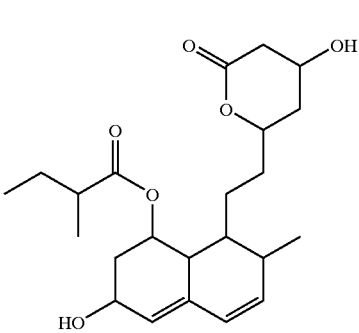
(VI-b)

(4) The process according to (1) above, wherein the compound (I-a) is a compound represented by the formula (VII-a) (herein referred to as compound (VII-a)):

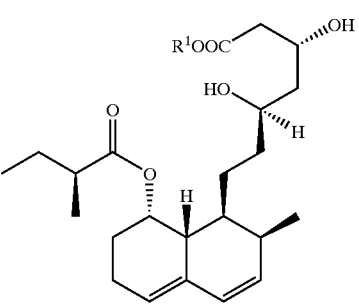
(VII-a)

the compound (I-b) is a compound represented by the formula (VII-b) (herein referred to as compound (VII-b)):

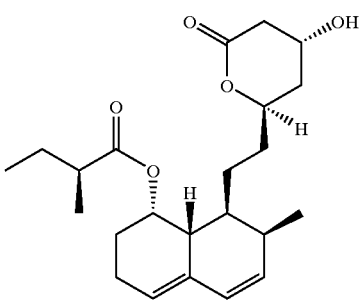
(VII-b)

the compound (II-a) is a compound represented by the formula (VIII-a) (herein referred to as compound (VIII-a)):

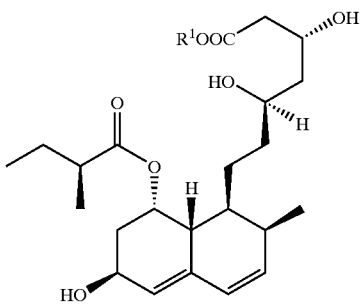

(VIII-a)

and, the compound (II-b) is a compound represented by the formula (VIII-b) (herein referred to as compound (VIII-b)):

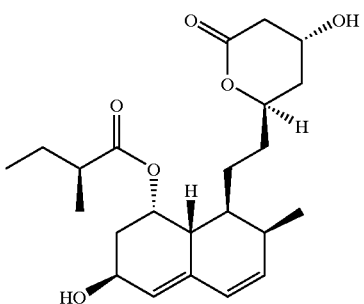

(VIII-b)

(5) The process according to (1), wherein the treated product of the culture of the microorganism is a treated product selected from cultured cells; treated products such as dried cells, freeze-dried cells, cells treated with a surfactant, cells treated with an enzyme, cells treated by ultrasonication, cells treated by mechanical milling, cells treated by solvent; a protein fraction of a cell; and an immobilized products of cells or treated cells.

(6) The process according to (1) above, wherein the microorganism is selected from those belonging to the genus *Mycobacterium, Corynebacterium, Brevibacterium, Rhodococcus, Gordonia, Arthrobacter, Micrococcus, Cellulomonas* and *Sphingomonas*.

(7) The processing according to (1) above, wherein the microorganism is one selected from *Mycobacterium phlei, Mycobacterium smegmatis, Mycobacterium thermoresistibile, Mycobacterium neoaurum, Mycobacterium parafortuitum, Mycobacterium gilvum, Rhodococcus globerulus, Rhodococcus equi, Rhodococcus erythropolis, Rhodococcus rhodochrous, Rhodococcus rhodnii, Rhodococcus ruber, Rhodococcus coprophilus, Rhodococcus fascians, Gordonia amarae, Gordonia rubropertinctus, Gordonia bronchialis, Gordonia sputi, Gordonia aichiensis, Gordonia terrae, Corynebacterium glutamicum, Corynebacterium mycetoides, Corynebacterium variabilis, Corynebacterium ammoniagenes, Arthrobacter crystallopoietes, Arthrobacter duodecadis, Arthrobacter ramosus, Arthrobacter sulfureus, Arthrobacter aurescens, Arthrobacter citreus, Arthrobacter globiformis, Brevibacterium acetylicum, Brevibacterium linens, Brevibacterium incertum, Brevibacterium iodinum, Micrococcus luteus, Micrococcus roseus, Cellulomonas cellulans, Cellulomonas cartae, Sphingomonas paucimobilis, Sphingomonas adhaesiva,* and *Sphingomonas terrae*.

(8) The process according to (1) above, wherein the microorganism is one selected from *Mycobacterium phlei* JCM5865, *Mycobacterium smegmatis* JCM5866, *Mycobacterium thermoresistibile* JCM6362, *Mycobacterium neoaurum* JCM6365, *Mycobacterium parafortuitum* JCM6367, *Mycobacterium gilvum* JCM6395, *Rhodococcus globerulus* ATCC25714, *Rhodococcus equi* ATCC21387, *Rhodococcus equi* ATCC7005, *Rhodococcus erythropolis* ATCC4277, *Rhodococcus rhodochrous* ATCC21430, *Rhodococcus rhodochrous* ATCC13808, *Rhodococcus rhodnii* ATCC35071, *Rhodococcus ruber* JCM3205, *Rhodococcus coprophilus* ATCC29080, *Rhodococcus fascians* ATCC12974, *Rhodococcus fascians* ATCC35014, *Gordonia amarae* ATCC27808, *Gordonia rubropertinctus* IFM-33, *Gordonia rubropertinctus* ATCC14352, *Gordonia bronchialis* ATCC25592, *Gordonia sputi* ATCC29627, *Gordonia aichiensis* ATCC33611, *Gordonia terrae* ATCC25594, *Corynebacterium glutamicum* ATCC13032, *Corynebacterium glutamicum* ATCC14020, *Corynebacterium glutamicum* ATCC19240, *Corynebacterium mycetoides* ATCC21134, *Corynebacterium variabilis* ATCC15753, *Corynebacterium ammoniagenes* ATCC6872, *Arthrobacter crystallopoietes* ATCC15481, *Arthrobacter duodecadis* ATCC13347, *Arthrobacter ramosus* ATCC13727, *Arthrobacter sulfureus* ATCC19098, *Arthrobacter aurescens* ATCC13344, *Arthrobacter citreus* ATCC11624, *Arthrobacter globiformis* ATCC8010, *Brevibacterium acetylicum* ATCC953, *Brevibacterium linens* ATCC19391, *Brevibacterium linens* ATCC9172, *Brevibacterium incertum* ATCC8363, *Brevibacterium iodinum* IFO3558, *Micrococcus luteus* ATCC4698, *Micrococcus roseus* ATCC186, *Cellulomonas cellulans* ATCC15921, *Cellulomonas cartae* ATCC21681, *Sphingomonas paucimobilis* ATCC29837, *Sphingomonas adhaesiva* JCM7370, and *Sphingomonas terrae* ATCC15098. The Institute for Fermentation (IFO), Osaka, is located at 17-85, Juso-honmachi, 2-chrome, Yodogawa-ku, Osaka 532-8686, Japan. The Japan Collection of Microorganisms (JCM), RIKEN (The Institute of Physical and Chemical Research), is located at 2-1 Hirosawa, Wako, Saitama 351-0198, Japan.

(9) The process according to (1) above, wherein the microorganism is *Gordonia* sp. ATCC19067.

The present invention is described in detail below.

Examples of an enzyme source used in the present invention include: a microorganism which has an activity of producing the above compound (II-a) or the above compound (II-b) from the above compounds (I-a) or the above compound (I-b), having no ability to sporulate and showing no hyphal growth; a culture of said microorganism; or a treated product of said culture.

Alkyl is a linear or branched alkyl containing 1 to 10 carbon atoms, preferably 1 to 6 carbon atoms, such as methyl, ethyl, propyl, isopropyl, butyl, isobutyl, sec-butyl, tert-butyl, pentyl, neopentyl, hexyl, isohexyl, heptyl, 4,4-dimethylpentyl, octyl, 2,2,4-trimethylpentyl, nonyl, decyl, and various branched chain isomers thereof.

Examples of aryl include phenyl and naphthyl.

The substituent of the substituted alkyl may be 1 to 3 identical or different groups, and examples thereof include halogens, hydroxy, amino, alkoxy and aryl.

The substituent of the substituted aryl may be 1 to 3 identical or different groups, and examples thereof include halogens, hydroxy, amino, alkyl and alkoxy.

The alkyl moiety of the alkoxy has the same definition as in the alkyl mentioned above.

Alkali metal represents each element of lithium, sodium, potassium, rubidium, cesium or francium.

Examples of the above microorganism include microorganisms selected from the genus *Mycobacterium,*

*Corynebacterium, Brevibacterium, Rhodococcus, Gordonia, Arthrobacter, Micrococcus, Cellulomonas* and *Sphingomonas*.

Specific examples include microorganisms selected from *Mycobacterium phlei, Mycobacterium smegmatis, Mycobacterium thermoresistibile, Mycobacterium neoaurum, Mycobacterium parafortuitum, Mycobacterium gilvum, Rhodococcus globerulus, Rhodococcus equi, Rhodococcus erythropolis, Rhodococcus rhodochrous, Rhodococcus rhodnii, Rhodococcus ruber, Rhodococcus coprophilus, Rhodococcus fascians, Gordonia amarae, Gordonia rubropertinctus, Gordonia bronchialis, Gordonia sputi, Gordonia aichiensis, Gordonia terrae, Corynebacterium glutamicum, Corynebacterium mycetoides, Corynebacterium variabilis, Corynebacterium ammoniagenes, Arthrobacter crystallopoietes, Arthrobacter duodecadis, Arthrobacter ramosus, Arthrobacter sulfureus, Arthrobacter aurescens, Arthrobacter citreus, Arthrobacter globiformis, Brevibacterium acetylicum, Brevibacterium linens, Brevibacterium incertum, Brevibacterium iodinum, Micrococcus luteus, Micrococcus roseus, Cellulomonas cellulans, Cellulomonas cartae, Sphingomonas paucimobilis, Sphingomonas adhaesiva*, and *Sphingomonas terrae*.

More specifically, examples include *Mycobacterium phlei* JCM5865, *Mycobacterium smegmatis* JCM5866, *Mycobacterium thermoresistibile* JCM6362, *Mycobacterium neoaurum* JCM6365, *Mycobacterium parafortuitum* JCM6367, *Mycobacterium gilvum* JCM6395, *Rhodococcus globerulus* ATCC25714, *Rhodococcus equi* ATCC21387, *Rhodococcus equi* ATCC7005, *Rhodococcus erythropolis* ATCC4277, *Rhodococcus rhodochrous* ATCC21430, *Rhodococcus rhodochrous* ATCC13808, *Rhodococcus rhodnii* ATCC35071, *Rhodococcus ruber* JCM3205, *Rhodococcus coprophilus* ATCC29080, *Rhodococcus fascians* ATCC12974, *Rhodococcus fascians* ATCC35014, *Gordonia amarae* ATCC27808, *Gordonia rubropertinctus* IFM-33, *Gordonia rubropertinctus* ATCC14352, *Gordonia bronchialis* ATCC25592, *Gordonia sputi* ATCC29627, *Gordonia aichiensis* ATCC33611, *Gordonia terrae* ATCC25594, *Corynebacterium glutamicum* ATCC13032, *Corynebacterium glutamicum* ATCC14020, *Corynebacterium glutamicum* ATCC19240, *Corynebacterium mycetoides* ATCC21134, *Corynebacterium variabilis* ATCC15753, *Corynebacterium ammoniagenes* ATCC6872, *Arthrobacter crystallopoietes* ATCC15481, *Arthrobacter duodecadis* ATCC13347, *Arthrobacter ramosus* ATCC13727, *Arthrobacter sulfureus* ATCC19098, *Arthrobacter aurescens* ATCC13344, *Arthrobacter citreus* ATCC11624, *Arthrobacter globiformis* ATCC8010, *Brevibacterium acetylicum* ATCC953, *Brevibacterium linens* ATCC19391, *Brevibacterium linens* ATCC9172, *Brevibacterium incertum* ATCC8363, *Brevibacterium iodinum* IFO3558, *Micrococcus luteus* ATCC4698, *Micrococcus roseus* ATCC186, *Cellulomonas cellulans* ATCC15921, *Cellulomonas cartae* ATCC21681, *Sphingomonas paucimobilis* ATCC29837, *Sphingomonas adhaesiva* JCM7370, *Sphingomonas terrae* ATCC15098 and *Gordonia* sp. ATCC19067.

In addition, a subculture, mutant, derivative or recombinant produced by a recombinant DNA technique of any of these microorganisms can also be used.

As a medium used for the culture of the microorganism used in the present invention, both natural and synthetic media can be used, as long as the media contain a carbon source, a nitrogen source, inorganic salts and the like which can be assimilated by the microorganism of the present invention, and can achieve an efficient culture of the microorganism of the present invention.

Specific examples of the carbon source in a medium include carbohydrates such as glucose, fructose, glycerol, maltose, starch and saccharose, and organic acids such as acetic acid and citric acid and molasses.

Specific examples of the nitrogen source include ammonia; ammonium salts of various types of inorganic acids and organic acids, such as ammonium chloride, ammonium sulfate, ammonium acetate, ammonium nitrate and ammonium phosphate; peptone, meat extract, corn steep liquor, casein hydrolysate, soybean meal, cottonseed meal, fish meal, various types of fermented microbial cells and digests thereof.

Specific examples of inorganic substances include potassium dihydrogenphosphate, dipotassium hydrogenphosphate, magnesium phosphate, magnesium sulfate, sodium chloride, ferrous sulfate, manganese sulfate, copper sulfate, and calcium carbonate.

Vitamins such as thiamin and biotin, amino acids such as glutamic acid and aspartic acid, nucleic acid-related substances such as adenine and guanine may be added, as required.

The culturing of the microorganism used in the present invention is preferably carried out under aerobic conditions such as a shaking culture, an aeration-agitation culture or the like. Where the aeration-agitation culture is applied, it is preferred to add an appropriate amount of antifoaming agent to prevent foaming. The culture is carried out usually at 20 to 50° C., preferably at 25 to 40° C., for 6 to 120 hours. During culturing, pH is maintained at 5.0 to 10.0, preferably at 6.0 to 8.5. The pH control is carried out by using inorganic or organic acid, an alkaline solution, urea, calcium carbonate, ammonia, etc.

Examples of a treated product of the thus-obtained cultured microorganism include cultured cells; a treated product such as dried cells, freeze-dried cells, cells treated with a surfactant, cells treated with an enzyme, cells treated by ultrasonication, cells treated by mechanical milling, cell treated by solvent; a protein fraction of cells; and an immobilized product of cells or treated cells.

The methods for converting compound (I-a) or compound (I-b) into compound (II-a) or compound (II-b) may be a method of previously adding compound (I-a) or compound (I-b) to a medium in which a microorganism is to be cultured, or may be a method of adding compound (I-a) or compound (I-b) during culturing. Further, a method of allowing an enzyme source to act upon compound (I-a) or compound (I-b) in an aqueous medium may also be used.

In a case where compound (I-a) or compound (I-b) is added to a medium in which a microorganism is to be cultured, 0.1 to 10 mg, preferably 0.2 to 1 mg of the compound (I-a) or the compound (I-b) is added to 1 ml of medium at the beginning of or at some midpoint of the culture. When compound (I-a) or compound (I-b) is added, it may be added after it is dissolved in a solvent such as methyl alcohol or ethyl alcohol.

In a case where a method of allowing an enzyme source to act upon compound (I-a) or compound (I-b) in an aqueous medium, the amount of enzyme to be used depends on the specific activity of the enzyme source or the like. For example, when a culture of a microorganism or a treated product of the culture is used as an enzyme source, 5 to 1,000 mg, preferably 10 to 400 mg of enzyme source is added per 1 mg of compound (I-a) or compound (I-b). The reaction is performed in an aqueous medium, preferably at 20 to 50° C., and particularly preferably at 25 to 40° C. The reaction period depends on the amount, specific activity, etc. of the enzyme source to be used, but it is usually 0.5 to 150 hours, preferably 1 to 72 hours.

Examples of an aqueous medium include water or buffers such as phosphate buffer, HEPES (N-2 hydroxyethylpiperazine-N-ethanesulfonate) buffer and Tris (tris(hydroxymethyl)aminomethane)hydrochloride buffer. An organic solvent may be added to the above buffers, unless it inhibits reaction. Examples of organic solvent include acetone, ethyl acetate, dimethyl sulfoxide, xylene, methyl alcohol, ethyl alcohol and butanol. A mixture of an organic solvent and an aqueous medium is preferably used when compound (I-b) is used.

According to the above production method, compound (II-b) or a mixture of compound (II-a) and compound (II-b) can be obtained from compound (I-a).

Similarly, compound (II-b) or a mixture of compound (II-a) and compound (II-b) can be obtained from compound (I-b).

Moreover, a mixture of compound (II-a) and compound (II-b) can be obtained from a mixture of compound (I-a) and compound (I-b).

Compound (I-b) and compound (II-b) can easily be converted into compound (I-a) and compound (II-a) respectively, by a method for opening a lactone ring as mentioned below. Likewise, compound (I-a) and compound (II-a) can easily be converted into compound (I-b) and compound (II-b) respectively, by a method for producing lactone as mentioned below.

Examples of a method for opening a lactone ring include a method which comprises dissolving compound (I-b) or compound (II-b) in an aqueous medium and adding thereto an acid or alkali. Examples of the aqueous medium include water and an aqueous solution containing salts, which does not inhibit the reaction, such as phosphate buffer, Tris buffer and the like. The above aqueous solution may contain an organic solvent such as methanol, ethanol, ethyl acetate and the like in a concentration which does not inhibit the reaction. Examples of acid include acetic acid, hydrochloric acid and sulfuric acid, and examples of alkali include sodium hydroxide, potassium hydroxide and ammonia.

Examples of a method for producing lactone include a method which comprises dissolving compound (I-a) or compound (II-a) in a non-aqueous solvent and adding thereto an acid or base catalyst. As long as the non-aqueous solvent is an organic solvent which does not substantially contain water and is capable of dissolving compound (I-a) or compound (II-a), any type of non-aqueous solvent can be used.

Examples of non-aqueous solvents include dichloromethane and ethyl acetate. As a catalyst, any catalyst can be used, as long as it catalyzes lactonization and does not show any actions other than lactonization on a substrate or a reaction product. Examples of the above catalyst include trifluoroacetic acid and p-toluenesulfonic acid. Reaction temperature is not particularly limited, but is preferably 0 to 100° C., and is more preferably 20 to 80° C.

After completion of the reaction, compound (II-a) or compound (II-b) can be collected from the above solution by ordinary methods used in the field of organic synthetic chemistry such as extraction with organic solvents, crystallization, thin-layer chromatography, high performance liquid chromatography, etc.

As a method for detecting and quantifying the compound (II-a) or the compound (II-b) obtained by the present invention, any method can be used, as long as the detection or quantification of compound (II-a) and/or compound (II-b) can be performed. Examples thereof include $^{13}$C-NMR spectroscopy, $^1$H-NMR spectroscopy, mass spectroscopy, high performance liquid chromatography (HPLC) etc.

There may be stereoisomers such as optical isomers for some compounds among compound (I-a), compound (I-b), compound (II-a) and compound (II-b). The present invention covers all possible isomers and mixtures thereof including these stereoisomers.

As compound (I-a), compound (III-a) is preferably, compound (V-a) is more preferable, and compound (VII-a) is particularly preferable.

As compound (I-b), compound (III-b) is preferable, compound (V-b) is more preferable, and compound (VII-b) is particularly preferable.

As compound (II-a), compound (IV-a) is preferable, compound (VI-a) is more preferable, and compound (VIII-a) is particularly preferable.

As compound (II-b), compound (IV-b) is preferable, compound (VI-b) is more preferable, and compound (VII-b) is particularly preferable.

The examples of the present invention is described below, but the present invention is not limited to these examples.

THE BEST MOST FOR CARRYING OUT THE INVENTION

EXAMPLE 1

100 mg of compound (VII-b) (produced by Sigma) was dissolved in 9.5 ml of methanol, and 0.5 ml of 1 mol/l sodium hydroxide was added. The mixture was stirred at room temperature for 1 hour. The obtained reaction solution was dried to be solidified, and was dissolved by adding 5 ml of deionized water, followed by adjusting pH to around 6.5 to 7.5 with about 0.1 ml of 1 mol/l hydrochloric acid. Then, 4.9 ml of deionized water was added to the mixture to obtain 10 ml of compound (VII-a), whose final concentration was 10 mg/ml (a compound wherein, in formula (VII-a), $R^1$ is sodium).

Various types of microorganisms shown in Tables 1 and 2 were independently plated onto an agar medium (1% peptone (produced by Kyokuto Pharmaceutical Industrial Co., Ltd.), 0.7% meat extract (produced by Kyokuto Pharmaceutical Industrial Co., Ltd.), 0.3% NaCl, 0.2% yeast extract (produced by Nihon Pharmaceutical Co., Ltd.), 2% bacto agar (produced by Difco), adjusted to pH7.2 with 1 mol/l sodium hydroxide), then cultured for 3 days at each temperature shown in Tables 1 and 2. An inoculating loop of each of the strains which grew on the agar medium was inoculated into a test tube containing 3 ml of LB medium (1% bacto tryptone (produced by Difco), 0.5% bacto yeast extract (produced by Difco), adjusted to pH7.2 with 1 mol/l sodium hydroxide). This tube was then subjected to shaking culture for 24 hours at each temperature shown in Tables 1 and 2. After culturing, 0.25 ml of the culture was inoculated in test tubes containing 5 ml of TB medium (1.4% bacto tryptone (produced by Difco), 2.4% bacto yeast extract (produced by Difco), 0.231% $KH_2PO_4$, 1.251% $K_2HPO_4$, adjusted to pH7.4 with 1 mol/l sodium hydroxide). The tubes were then subjected to shaking culture for 24 hours at each temperature shown in Tables 1 and 2. After 24 hours, the above-obtained compound (VII-a) was added to each of test tubes in a the final concentration of 0.4 mg/ml, and then reaction was performed with shaking at each temperature shown in Tables 1 and 2 for 48 hours.

After completion of the reaction, the reaction solution was adjusted to pH3.5 with acetic acid. 1 ml of ethyl acetate was added to 0.5 ml of this reaction solution followed by shaking for 1 hour. After shaking, the reaction solution was separated into 2 layers by centrifugation at 3,000 rpm for 5 minutes, then the upper ethyl acetate layer was collected. The solvent was removed with a centrifugal evaporator, and the residue was dissolved in 0.5 ml of methanol. Using a portion of this methanol solution, HPLC analysis was carried out (Column: Inertsil ODS-2 (5 μm, 4×250 mm, produced by GL Science), Column temperature: 60° C., Mobile phase: acetonitrile:water:phosphoric acid=55:45:0.05, Flow rate: 0.9 ml/min, Detection wavelength: 237 nm), to detect and quantify compound (VIII-a) (a compound wherein, in formula (VIII-a), $R^1$ is sodium). The results are shown in Tables 1 and 2.

TABLE 1

| Strain | | Compound (VIII-a) mg/l | Culturing Temperature (° C.) |
|---|---|---|---|
| Mycobacterium phlei | JCM 5865 | 1.6 | 37 |
| Mycobacterium smegmatis | JCM 5866 | 0.4 | 37 |
| Mycobacterium thermoresistibile | JCM 6362 | 9.1 | 37 |
| Mycobacterium neoaurum | JCM 6365 | 3.7 | 37 |
| Mycobacterium parafortuitum | JCM 6367 | 7.4 | 37 |
| Mycobacterium gilvum | JCM 6395 | 9.6 | 37 |
| Rhodococcus globerulus | ATCC25714 | 4.9 | 28 |
| Rhodococcus equi | ATCC21387 | 2.5 | 30 |
| Rhodococcus erythropolis | ATCC4277 | 1.4 | 30 |
| Rhodococcus rhodochrous | ATCC21430 | 4.9 | 30 |
| Rhodococcus equi | ATCC7005 | 1.4 | 30 |
| Rhodococcus rhodochrous | ATCC13808 | 4.7 | 28 |
| Rhodococcus rhodnii | ATCC35071 | 0.4 | 28 |
| Rhodococcus ruber | JCM 3205 | 0.6 | 28 |
| Rhodococcus coprophilus | ATCC29080 | 5.6 | 28 |
| Rhodococcus fascians | ATCC12974 | 1.3 | 28 |
| Rhodococcus fascians | ATCC35014 | 5.2 | 30 |
| Gordona amarae | ATCC27808 | 1.2 | 30 |
| Gordona rubropertinctus | IFM-33 | 2.5 | 30 |
| Gordona bronchialis | ATCC25592 | 0.9 | 28 |
| Gordona rubropertinctus | ATCC14352 | 0.7 | 28 |
| Gordona sputi | ATCC29627 | 0.3 | 28 |
| Gordona aichiensis | ATCC33611 | 0.6 | 28 |
| Gordona sp. | ATCC19067 | 4.0 | 30 |
| Gordona terrae | ATCC25594 | 0.3 | 28 |

TABLE 2

| Strain | | Compound (VIII-a) mg/l | Culturing Temperature (° C.) |
|---|---|---|---|
| Corynebacterium glutamicum | ATCC13032 | 1.1 | 30 |
| Corynebacterium glutamicum | ATCC14020 | 0.7 | 30 |
| Corynebacterium glutamicum | ATCC19240 | 1.0 | 30 |
| Corynebacterium mycetoides | ATCC21134 | 0.3 | 30 |
| Corynebacterium variabilis | ATCC15753 | 1.7 | 30 |
| Corynebacterium ammoniagenes | ATCC6872 | 0.6 | 30 |
| Arthrobacter crystallopoietes | ATCC15481 | 0.5 | 30 |
| Arthrobacter duodecadis | ATCC13347 | 0.7 | 30 |
| Arthrobacter ramosus | ATCC13727 | 2.2 | 30 |
| Arthrobacter sulfureus | ATCC19098 | 1.1 | 30 |
| Arthrobacter aurescens | ATCC13344 | 1.3 | 30 |
| Arthrobacter citreus | ATCC11624 | 1.2 | 30 |
| Arthrobacter globiformis | ATCC8010 | 0.3 | 30 |
| Brevibacterium acetylicum | ATCC953 | 0.4 | 30 |
| Brevibacterium linens | ATCC19391 | 0.5 | 30 |
| Brevibacterium linens | ATCC9172 | 0.6 | 30 |
| Brevibacterium incertum | ATCC8363 | 0.5 | 30 |
| Brevibacterium iodinum | IFO3558 | 0.8 | 30 |
| Micrococcus luteus | ATCC4698 | 0.5 | 30 |
| Micrococcus roseus | ATCC186 | 0.4 | 30 |
| Cellulomonas cellulans | ATCC15921 | 0.7 | 30 |
| Cellulomonas cartae | ATCC21681 | 0.7 | 30 |
| Sphingomonas paucimobilis | ATCC29837 | 3.4 | 30 |
| Sphingomonas adhaesiva | JCM 7370 | 2.7 | 37 |
| Sphingomonas terrae | ATCC15098 | 3.1 | 30 |

EXAMPLE 2

*Mycobacterium gilvum* JCM 6395 strain was plated onto the same agar medium as in Example 1 and was cultured at 37° C. for 3 days. The strain which grew on the agar medium was inoculated into 4 test tubes each containing 3 ml of LB medium, followed by shaking culture at 37° C. for 24 hours. 1.25 ml of each of the cultures was inoculated into eight 300-ml Erlenmeyer flasks containing 25 ml of TB medium, followed by shaking culture at 37° C. After 24 hours, compound (VII-a) prepared as in Example 1 (a compound wherein, in formula (VII-a), $R^1$ is sodium) was added in the final concentration of 0.4 mg/ml, and the mixture was shaken at 37° C. for 48 hours. After completion of the reaction, the culture was centrifuged at 3,000 rpm at 4° C. for 10 minutes to collect the supernatant. The pH of this supernatant was adjusted to 3.5 with acetic acid. After 400 ml of ethyl acetate was added thereto, the mixture was shaken at 30° C. for 1 hour. After leaving to stand, supernatant was collected. The same operation was repeated to the aqueous lower layer, then the obtained ethyl acetate layer was combined with the aforementioned supernatant. After 100 ml of saturated saline solution was added to this ethyl acetate layer, the mixture was shaken, and supernatant was collected.

Next, 5 g of anhydrous $Na_2SO_4$ was added to this supernatant and the mixture was left at room temperature for 15 minutes. Then, ethyl acetate was evaporated under reduced pressure so that the mixture was solidified. The obtained residue was dissolved in 5 ml of deionized water, and pH was adjusted to 9.0 with sodium hydroxide, followed by passing the solution through a 50 ml HP-20 column (25×100 mm, produced by Mitsubishi Chemical Corp.) After washing the column with 150 ml of deionized water, elution was carried out in a stepwise manner with 100 ml of acetone solutions each of which contains 20%, 30% and 40% acetone. The collected fractions were subjected to the same HPLC analysis as in Example 1, thereby recovering a fraction containing compound (VIII-a). Acetonitrile was removed from this fraction under reduced pressure, then pH of the solution was adjusted to 3.0 with 1 mol/l hydrochloric acid. After 360 ml of ethyl acetate was added to this solution, the mixture was shaken. After leaving to stand, supernatant was collected. After 90 ml of saturated saline solution was added to this supernatant, the mixture was shaken, and left to stand, and the supernatant was collected.

Subsequently, 4.5 g of anhydrous $Na_2SO_4$ was added to this supernatant and the mixture was left at room temperature for 15 minutes followed by evaporating to dryness under reduced pressure. The obtained dried residue was dissolved in dichloromethane and lactonized by adding 1% trifluoroacetic acid. This reaction product was fractionated with preparative TLC (Silica gel plate: No. 1.05744 (200× 200 mm, thickness: 0.5 mm, produced by Merck), development solvent: ethyl acetate, color-development solution: 12.5% phosphomolybdic acid-1% cerium/10% sulfuric acid solution), thereby obtaining 0.8 mg of compound (VIII-b). The results of mass spectrum and $^1$H-NMR spectrum analyses of the obtained compound (VIII-b) are as follows.

Mass Spectrum

Applying JMS-HX/HX110A mass spectrometer (manufactured by NIHON DENSHI Ltd.), the measurement was done in a positive mode using m-nitrobenzyl alcohol as a matrix. As a result, a pseudoion peak ($[M+H]^+$) was obtained at m/z 407, and the actual measurement value matched with the value expected from the structure and molecular weight (406) of compound (II-b).

¹H-NMR Spectrum

Applying type JNM-α400 spectrometer (manufactured by NIHON DENSHI Ltd.), the measurement was done at 400 MHz in duetero chloroform, using TMS as an internal standard. The results are shown below. The spectrum data were consistent with the known data regarding compound (VIII-b) (*Sanko Research Laboratories Annual Report*, 37, 147 (1985).

δ ppm (CDCl$_3$): 6.01 (1H, d, J=9.5 Hz), 5.89 (1H, dd, J=9.5, 5.9 Hz), 5.58 (1H, m), 5.41 (1H, m), 4.60 (1H, ddd, J=10.6, 7.3, 5.4, 2.8 Hz), 4.40 (1H, m), 4.38 (1H, m), 2.74 (1H, dd, J=13.1, 6.0, 4.8, 1.5 Hz), 2.40 (1H, m), 2.36 (1H, m), 2.34 (1H, m), 1.95 (1H, dddd, J=14.4, 3.7, 2.9, 1.7 Hz), 1.86 (1H, dddd, J=12.5, 12.3, 7.3, 4.3 Hz), 1.69 (1H, m), 1.68 (1H, m), 1.64 (1H, m), 1.57 (1H, m), 1.5–1.4 (2H, m), 1.43 (1h, m), 1.30 (1H, m), 1.12 (3H, d, J=6.8 Hz), 0.91 (3H, d, J=7.1 Hz), 0.89 (3H, t, J=7.4 Hz).

Industrial Applicability

According to the present invention, it becomes possible to efficiently produce a compound, which inhibits HMG-CoA reductase and has an action of reducing the level of serum cholesterol.

What is claimed is:

1. A process for producing a compound (II-a) or a compound (II-b) wherein a microorganism having an activity of producing compound (II-a) or a compound (II-b) from a compound (I-a) or a compound (I-b), selected from the group consisting of those belonging to the genus *Mycobacterium, Corynebacterium, Brevibacterium, Rhodococcus, Gordonia, Arthrobacter, Micrococcus, Cellulomonas* and *Sphingomonas*, a culture of said microorganism, or a treated product of said culture used as an enzyme source, the process comprising: allowing the compound (I-a) or the compound (I-b) to exist in an aqueous medium; allowing the compound (II-a) or the compound (II-b) to be produced and accumulated to said aqueous medium; and collecting the compound (II-a) or the compound (II-b) from said aqueous medium, and wherein the compound (I-a) is a compound represented by the formula (I-a):

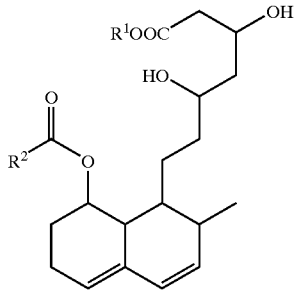

(I-a)

wherein R$^1$ represents a hydrogen atom, a substituted or unsubstituted alkyl, or an alkali metal, and R$^2$ represents a substituted or unsubstituted alkyl, or a substituted or unsubstituted aryl;

the compound (I-b) is a lactone form of compound (I-a) represented by the formula (I-b):

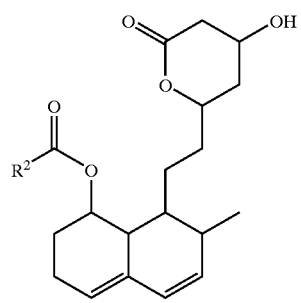

(I-b)

wherein R$^2$ has the same definition as the above;
the compound (II-a) is a compound represented by the formula (II-a):

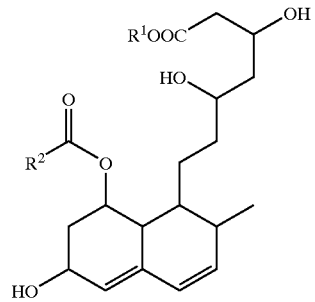

(II-a)

wherein R$^1$ and R$^2$ have the same definitions as the above; and
the compound (II-b) is a lactone form of compound (II-a) represented by the formula (II-b):

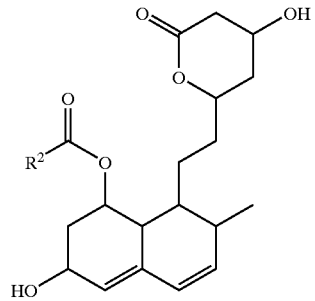

(II-b)

wherein R$^2$ has the same definition as the above; and
wherein the microorganism is one selected from *Mycobacterium phlei, Mycobacterium smegmatis, Mycobacterium thermoresistibile, Mycobacterium neoaurum, Mycobacterium parafortuitum, Mycobacterium gilvum, Rhodococcus globerulus, Rhodococcus equi, Rhodococcus erythropolis, Rhodococcus rhodochrous, Rhodococcus rhodnii, Rhodococcus ruber, Rhodococcus coprophilus, Rhodococcus fascians, Gordonia amarae, Gordonia bronchialis, Gordonia aichiensis, Gordonia terrae, Gordonia rubropertinctus, Gordonia sputi, Corynebacterium glutamicum, Corynebacterium mycetoides, Corynebacterium variabilis, Corynebacterium ammoniagenes, Arthrobacter crystallopoietes, Arthrobacter duodecadis, Arthrobacter ramosus, Arthrobacter sulfureus, Arthrobacter aurescens, Arthrobacter citreus, Arthrobacter globiformis, Brevibacterium linens, Brevibacterium iodinum, Micrococcus luteus, Micrococcus roseus, Cellulomonas cellulans, Cellulomonas cartae, Sphingomonas paucimobilis, Sphingomonas adhaesiva*, and *Sphingomonas terrae*.

2. The process according to claim 1, wherein the compound (I-a) is a compound represented by the formula (III-a):

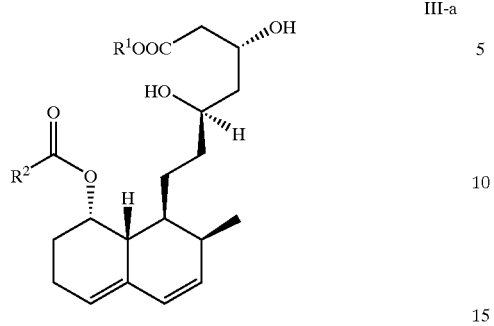

III-a wherein $R^1$ represents a hydrogen atom, a substituted or unsubstituted alkyl, or an alkali metal, and $R^2$ represents a substituted or unsubstituted alkyl, or a substituted or unsubstituted aryl;
the compound (I-b) is a compound represented by the formula (III-b):

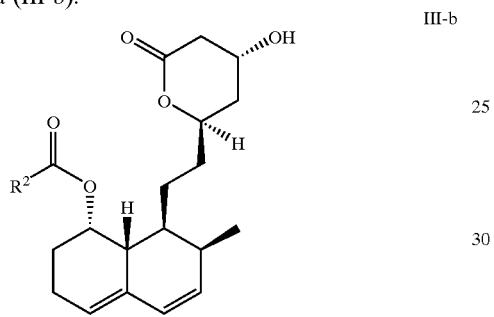

III-b wherein $R^2$ has the same definition as the above;
the compound (II-a) is a compound represented by the formula (IV-a):

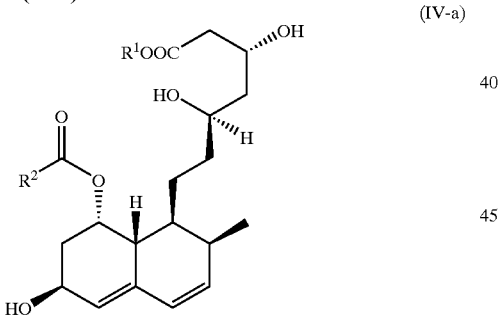

(IV-a)

wherein $R^1$ and $R^2$ have the same definitions as the above; and
the compound (II-b) is a compound represented by the formula (IV-b):

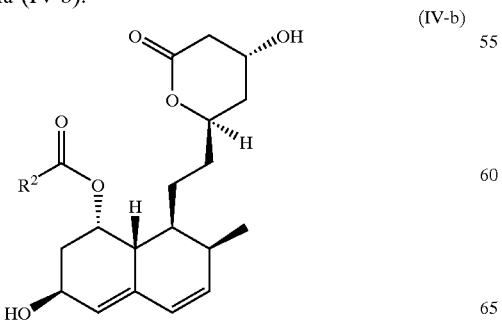

(IV-b)

wherein $R^2$ has the same definition as the above.

3. The process according to claim 1, wherein the compound (I-a) is a compound represented by the formula (V-a):

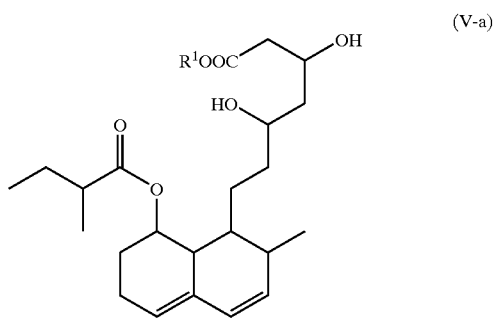

(V-a)

wherein $R^1$ represents a hydrogen atom, a substituted or unsubstituted alkyl, or an alkali metal;
the compound (I-b) is a compound represented by the formula (V-b);

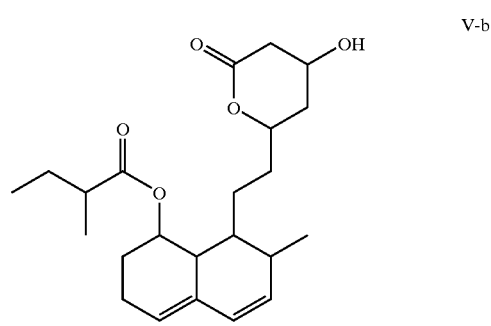

V-b the compound (II-a) is a compound represented by the formula (VI-a):

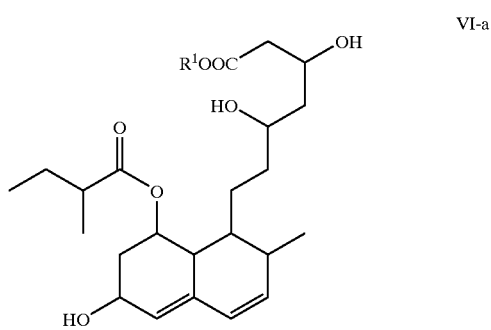

VI-a wherein $R^1$ has the same definition as the above; and
the compound (II-b) is a compound represented by the formula (VI-b):

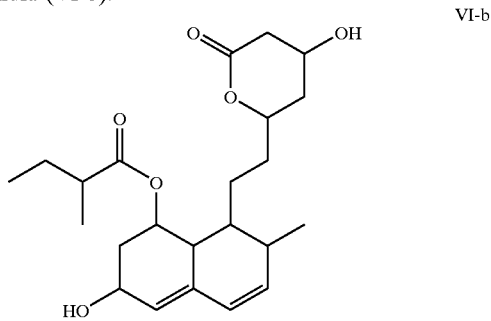

VI-b

4. The process according to claim 1, wherein the compound (I-a) is a compound represented by the formula (VII-a:

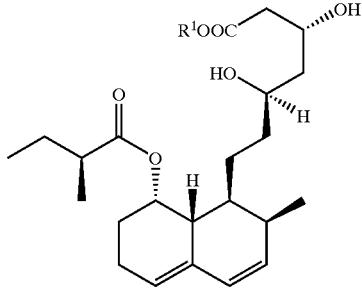

VII-a wherein R¹ represents a hydrogen atom, a substituted or unsubstituted alkyl, or an alkali metal;
the compound (I-b) is a compound represented by the formula (VII-b):

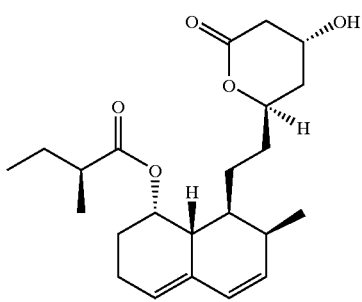

VII-b the compound (II-a) is a compound represented by the formula (VIII-a):

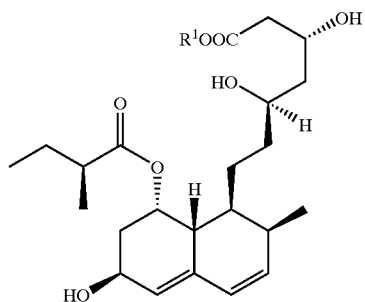

(VIII-a)

wherein R¹ has the same definition as the above; and
the compound (II-b) is a compound represented by the formula (VIII-b):

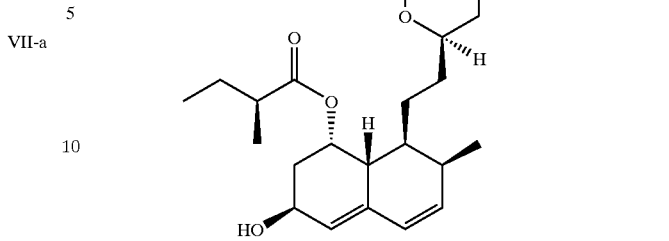

VIII-b

5. The process according to claim 1, wherein the treated product of the culture of the microorganism is a treated product selected from dried cells, freeze-dried cells, cells treated with a surfactant, cells treated with an enzyme, cells treated by ultrasonication, cells treated by mechanical milling, cells treated by solvent; and a protein fraction of a cell.

6. The process according to claim 1, wherein the microorganism is one selected from *Mycobacterium phlei* JCM5865, *Mycobacterium smegmatis* JCM5866, *Mycobacterium thermoresistibile* JCM6362, *Mycobacterium neoaurum* JCM6365, *Mycobacterium parafortuitum* JCM6367, *Mycobacterium gilvum* JCM6395, *Rhodococcus globerulus* ATCC25714, *Rhodococcus equi* ATCC21387, *Rhodococcus equi* ATCC7005, *Rhodococcus erythropolis* ATCC4277, *Rhodococcus rhodochrous* ATCC21430, *Rhodococcus rhodochrous* ATCC13808, *Rhodococcus rhodnii* ATCC35071, *Rhodococcus ruber* JCM3205, *Rhodococcus coprophilus* ATCC29080, *Rhodococcus fascians* ATCC12974, *Rhodococcus fascians* ATCC35014, *Gordonia amarae* ATCC27808, *Gordonia rubropertinctus* ATCC14352, *Gordonia bronchialis* ATCC25592, *Gordonia sputi* ATCC29627, *Gordonia aichiensis* ATCC33611, *Gordonia terrae* ATCC25594, *Corynebacterium glutamicum* ATCC13032, *Corynebacterium glutamicum* ATCC14020, *Corynebacterium glutamicum* ATCC19240, *Corynebacterium mycetoides* ATCC21134, *Corynebacterium variabilis* ATCC15753, *Corynebacterium ammoniagenes* ATCC6872, *Arthrobacter crystallopoietes* ATCC15481, *Arthrobacter duodecadis* ATCC13347, *Arthrobacter ramosus* ATCC13727, *Arthrobacter sulfureus* ATCC19098, *Arthrobacter aurescens* ATCC13344, *Arthrobacter citreus* ATCC11624, *Arthrobacter globiformis* ATCC8010, *Brevibacterium linens* ATCC19391, *Brevibacterium linens* ATCC9172, *Brevibacterium iodinum* IFO3558, *Micrococcus luteus* ATCC4698, *Micrococcus roseus* ATCC186, *Cellulomonas cellulans* ATCC15921, *Cellulomonas cartae* ATCC21681, *Sphingomonas paucimobilis* ATCC29837, and *Sphingomonas adhaesiva* JCM7370.

7. The process according to claim 1, wherein the microorganism is *Rhodococcus rhodochrous*, sp. ATCC19067.

* * * * *

UNITED STATES PATENT AND TRADEMARK OFFICE
CERTIFICATE OF CORRECTION

PATENT NO. : 6,946,270 B1
DATED : September 20, 2005
INVENTOR(S) : S. Hashimoto et al.

It is certified that error appears in the above-identified patent and that said Letters Patent is hereby corrected as shown below:

Column 15,
Line 42, "to said" should be -- in said --.

Signed and Sealed this

Twenty-third Day of May, 2006

JON W. DUDAS
*Director of the United States Patent and Trademark Office*